United States Patent [19]

Unger

[11] Patent Number: 5,149,319

[45] Date of Patent: Sep. 22, 1992

[54] METHODS FOR PROVIDING LOCALIZED THERAPEUTIC HEAT TO BIOLOGICAL TISSUES AND FLUIDS

[76] Inventor: Evan C. Unger, 13365 E. Camino La Cebadilla, Tucson, Ariz. 85749

[21] Appl. No.: 581,027

[22] Filed: Sep. 11, 1990

[51] Int. Cl.⁵ ............................................. A61B 17/20
[52] U.S. Cl. ................................. 604/22; 128/660.01; 128/24 AA; 424/7.1; 600/10
[58] Field of Search ............... 604/22, 20; 128/660.01, 128/660.02, 660.03, 660.07, 662.02, 653, 804, 24 EL, 24 R, 24 AA; 424/2, 7.1, 9; 73/194 A; 600/10, 12

[56] References Cited

U.S. PATENT DOCUMENTS

| | | | |
|---|---|---|---|
| 4,315,514 | 2/1982 | Drewes et al. | 128/653 R |
| 4,569,836 | 2/1986 | Gordon | 600/4 |
| 4,586,512 | 5/1986 | Do-huu et al. | 128/660 |
| 4,620,546 | 11/1986 | Aide et al. | 128/24 A |
| 4,646,756 | 3/1987 | Watmough et al. | 128/24 AA |
| 4,657,756 | 4/1987 | Rasor et al. | 424/9 |
| 4,689,986 | 9/1987 | Carson et al. | 73/19 |
| 4,865,836 | 9/1989 | Long, Jr. | 424/5 |
| 4,893,624 | 1/1990 | Lele | 128/24 AA |
| 4,900,540 | 2/1990 | Ryan et al. | 424/9 |

FOREIGN PATENT DOCUMENTS

WO8002365  11/1980  PCT Int'l Appl. ............ 128/662.02
WO8201642   5/1982  PCT Int'l Appl. ............ 128/662.02

OTHER PUBLICATIONS

Shinna et al., "Hyperthermia by low-frequency synthesized ultrasound" IEEE Engineering pp. 879–880 vol. 2 (abstract only).

Hunynen et al., "Temperature Distributions during local ultrasound induced hyperthermia in vivo" Ultrasonics Syposium Proceedings, pp. 745–749 vol. 2 (abstract only).

McAvay et al., *IEEE* 1989 Ultrasonic Symposium, Ultrasonics Symposium proceedings vol. 2 1989 pp. 677–1248 (abstract only).

*Primary Examiner*—C. Fred Rosenbaum
*Assistant Examiner*—Chalin Smith
*Attorney, Agent, or Firm*—Woodcock Washburn Kurtz Mackiewicz & Norris

[57] ABSTRACT

Gas, gaseous precursors and prefluorocarbons are presented as novel potentiators for ultrasonic hyperthermia. The gas, gaseous precursors and perfluorocarbons which may be administered into the vasculature, interstitially or into any body cavity are designed to accumulate in cancerous and diseased tissues. When therapeutic ultrasonic energy is applied to the diseased region heating is increased because of the greater effectiveness of sound energy absorption caused by these agents.

14 Claims, 2 Drawing Sheets

METHODS FOR PROVIDING LOCALIZED THERAPEUTIC HEAT TO BIOLOGICAL TISSUES AND FLUIDS

BACKGROUND OF THE INVENTION

1. Field of the Invention

The present invention relates to the use of ultrasonic energy to heat biological tissues and fluids, and more specifically, to the use of hyperthermia potentiators, such as gases, gaseous precursors and perfluorocarbons, in combination with ultrasound to facilitate the selective heating of the tissues and fluids.

2. Description of the Prior Art

The usefulness of heat to treat various inflammatory and arthritic conditions has long been known. The use of ultrasound to generate such heat for these as well as other therapeutic purposes, such as in, for example, the treatment of tumors has, however, been a fairly recent development.

Where the treatment of inflammation and arthritis is concerned, the use of the ultrasound induced heat serves to increase blood flow to the affected regions, resulting in various beneficial effects. Moreover, when ultrasonic energy is delivered to a tumor, the temperature of the tumorous tissue rises, generally at a higher rate than in normal tissue. As this temperature reaches above about 43° C., the tumorous cells begin to die and, if all goes well, the tumor eventually disappears. Ultrasound induced heat treatment of biological tissues and fluids is known in the art as hyperthermic ultrasound.

The non-invasive nature of the hyperthermia ultrasound technique is one of its benefits. Nonetheless, in employing hyperthermic ultrasound, certain precautions must be taken. Specifically, one must be careful to focus the ultrasound energy on only the areas to be treated, in an attempt to avoid heat-induced damage to the surrounding, non-targeted, tissues. In the treatment of tumors, for example, when temperatures exceeding about 43° C. are reached, damage to the surrounding normal tissue is of particular concern. This concern with over heating the non-target tissues thus places limits on the use of hyperthermic ultrasound. Such therapeutic treatments would clearly be more effective and more widely employed if a way of targeting the desired tissues and fluids, and of maximizing the heat generated in those targeted tissues, could be devised.

The present invention is directed toward improving the effectiveness and utility of hyperthermic ultrasound by providing agents capable of promoting the selective heating of targeted tissues and body fluids.

SUMMARY OF THE INVENTION

The present invention is directed to a method for heat treating biological tissues and fluids which comprises administering to the tissue or fluid to be treated a therapeutically effective amount of a hyperthermia potentiator, and then applying ultrasound to that tissue or fluid.

By using the potentiators of the present invention, hyperthermic ultrasound becomes a better, more selective and more effective therapeutic method for the treatment of tumors, inflammation, and arthritis, as well as other various conditions.

DETAILED DESCRIPTION OF THE INVENTION

Figure 1:
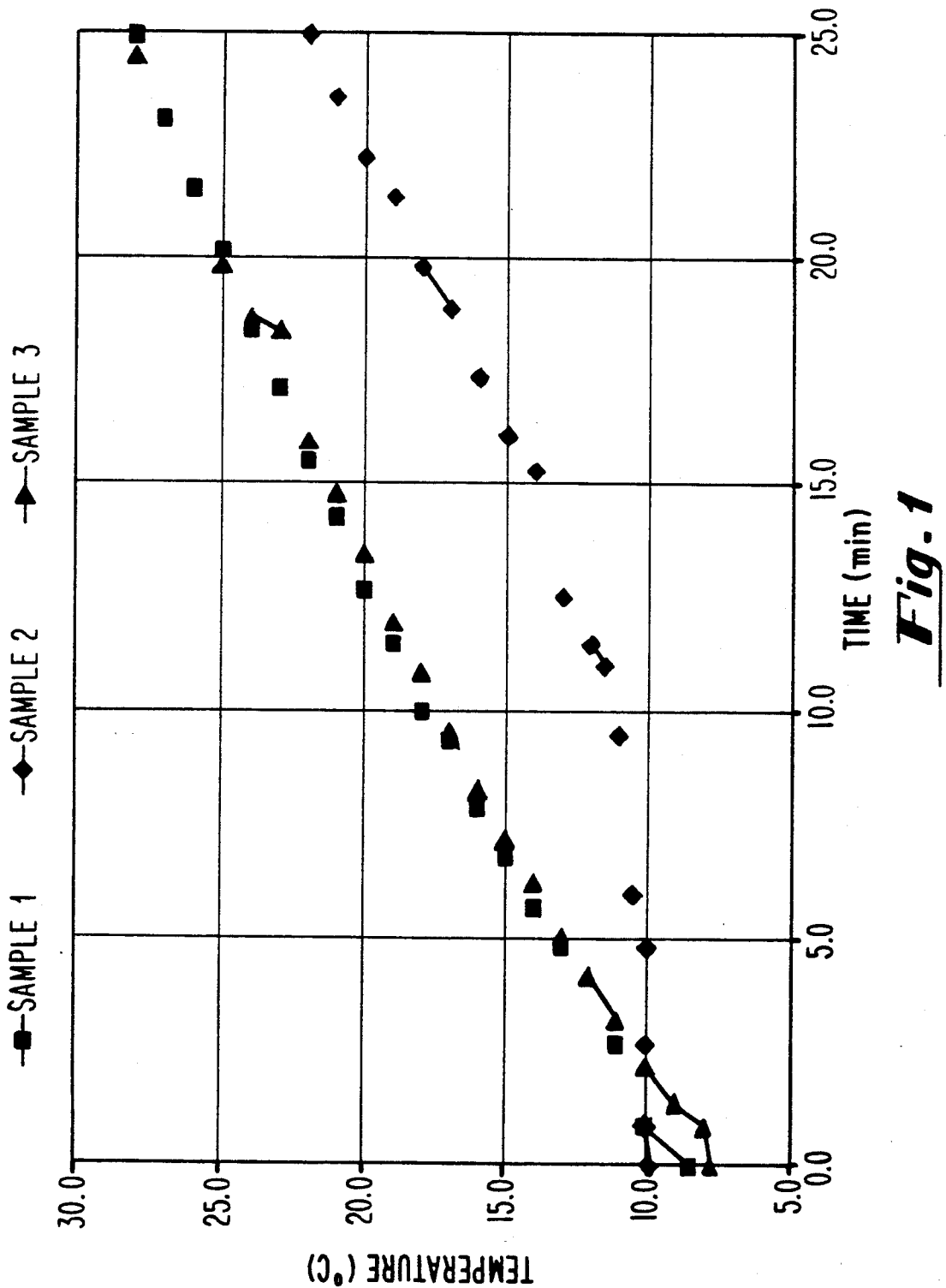
FIG. 1. This figure provides a graph which plots the temperature over time for three different samples subjected to ultrasound treatment using a 1.0 megahertz continuous wave source of ultrasonic energy. Both Sample 1 (multilamellar vesicles composed of egg phosphatidylcholine and having encapsulated therein $CO_2$ gas) and Sample 3 (a phosphate buffered saline solution pressurized With $CO_2$ gas) have a similar increase in temperature over time. Sample 2 (a degassed phosphate buffered saline solution) exhibited a much lower increase in temperature over time, as compared with Samples 1 and 3.

The present invention is directed to a method for heat treating biological tissues and fluids comprising administering to the tissues or fluids to be treated a therapeutically effective amount of a hyperthermia potentiator, and then applying ultrasound to said tissue or fluid.

As used herein the phrase "hyperthermia potentiator" denotes any biocompatible solid, liquid or gas capable of increasing the rate of ultrasound induced heating in biological tissues and fluids to which it is administered. Preferably, the hyperthermia potentiator is selected from the group consisting of gas, gaseous precursors and perfluorocarbons.

Any and all biocompatible gases may be employed as hyperthermia potentiators in the subject method. Preferably, however, the gas employed is air, carbon dioxide, oxygen, nitrogen, xenon, argon, neon or helium, or any and all combinations thereof. Preferably the gas is in the form of stabilized gas bubbles. The gas bubbles may be stabilized by a number of different means well-known to those skilled in the art. In the most preferred embodiment, the gas employed as the hyperthermia potentiator is air and the air is provided in the form of stabilized air bubbles.

Gaseous precursors can also be employed as hyperthermia potentiators in the present method. The gaseous precursors may be of various types, and include temperature sensitive, pressure sensitive, photo sensitive, and pH sensitive gaseous precursors which are designed to form gas either before or after administration to the biological tissue or fluid being treated. Such gaseous precursors have the advantage of being more stable on long-term storage than in many cases the gases themselves, including the stabilized gas bubbles.

The phrase "pH sensitive gaseous precursor", as used herein, denotes a compound in solid or liquid form which, when exposed to a change in pH, will form a gas. Such compounds include, but are not limited to, metal carbonate and bicarbonate salts, such as the alkali metal carbonates and bicarbonates, and the alkaline earth carbonates and bicarbonates, and mixtures thereof. Exemplary of such compounds are lithium carbonate, sodium carbonate, potassium carbonate, lithium bicarbonate, sodium bicarbonate, potassium bicarbonate, magnesium carbonate, calcium carbonate, magnesium bicarbonate, and the like. Also useful gas generating compounds are ammonium carbonate, ammonium bicarbonate, ammonium sesquecarbonate, sodium sesquecarbonate, and the like. These compounds, when dissolved in water, show a pH of greater than about 7, usually between about 8 and about 12. Other pH-activated gaseous precursors include aminomalonate, which, when dissolved in water, generally shows a pH of about 5 to 6. The pka1 of aminomalonate is 3.32 and the pka2 is 9.83. Aminomalonate is well known in the art, and its preparation is described, for example, in Thanassi, *Biochemistry*, Vol. 9, no. 3, pp. 525-532 (1970), Fitzpatrick et al., *Inorganic Chemistry*, Vol. 13, no. 3, pp. 568-574 (1974), Stelmashok et al., *Koordinatsionnaya Khimiya*, Vol. 3, no. 4, pp. 524-527 (1977). Other suitable pH sensitive gaseous precursors will be apparent to those skilled in the art.

As those skilled in the art would recognize, such compounds can be activated prior to administration, if desired. Of course by choosing a gaseous precursor with the appropriate pKa, one skilled in the art can prepare a formulation that will form a gas after it has been administered to the biological tissues or fluids. The pH sensitive gaseous precursors, for example, may form gas at a site with lower pH such as in a hypoxic, acidic tumor, or may simply form a gas upon exposure to physiological pH.

As used herein, the phrase "photo sensitive gaseous precursor" denotes a light sensitive compound in solid or liquid form which becomes a gas after exposure to such light. Suitable photosensitive compounds include diazonium compounds which decompose to form nitrogen gas after exposure to ultraviolet light. Another suitable compound is aminomalonate. As one skilled in the art would recognize, other gaseous precursors may be chosen which form gas after exposure to light. Depending upon the application, exposure to such light may be necessary prior to administration, or in some instances can occur subsequent to administration.

As used herein, the phrase "temperature sensitive gaseous precursor" denotes a solid or liquid compound which forms a gas following a change in temperature. Suitable temperature sensitive gaseous precursors are well known to those skilled in the art, and include, for example, methylactate, a compound which is in a liquid phase at ambient temperatures, but which forms a gas at physiological temperatures. As those skilled in the art would recognize, such compounds can be activated prior to administration or, as in the case of methylactate, can be activated upon administration at physiological temperatures or as a result of the ultrasound induced hyperthermia.

Of all of the possible gaseous precursors, the most preferred gaseous precursors for use with the present invention are those selected from the group consisting of aminomalonate, sodium bicarbonate, methylactate and diazonium compounds, including any and all combinations thereof.

The hyperthermia potentiators employed in the method of the subject invention may also comprise one or more perfluorocarbons, preferably a perfluorocarbon compound selected from the group consisting of perfluorooctyliodide, perfluorotributylamine, perfluorotripropylamine and perfluorooctlybromide, and any and all combinations thereof. Preferably the perfluorocarbons are administered in the form of an emulsion. Such emulsions are particularly desirable when using perfluorocarbons for intravascular injection to avoid uptake by the pulmonary vasculature. For such uses, the emulsion particles should be smaller than 5 microns in size to allow passage through the pulmonary microcirculation. The art of preparing emulsions is well-known, and the subject perfluorocarbon emulsions can be prepared in any conventional fashion, such as by those procedures shown in U.S. Pat. No. 4,865,836 for the preparation of perfluorocarbon emulsions, the disclosures of which are incorporated herein by reference in their entirety.

If desired, the hyperthermia potentiators, such as the gases, gaseous precursors and perfluorocarbons described herein, may be encapsulated in liposomes prior to administration, or may be otherwise stabilized. Stabilized gas bubbles are particularly preferred. The phrase stabilized gas bubbles, as used herein, refers to any construct wherein the release of gas bubbles is prevented, constrained or modulated.

Liposomes may be prepared using any one or a combination of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. No. 4,728,575, U.S. Pat. No. 4,737,323, International Application PCT/US85/01161, Mayer et al., *Biochimica et Biophysica Acta*, Vol. 858, pp. 161-168 (1986), Hope et al., *Biochimica et Biophysica Acta*, Vol. 812, pp. 55-65 (1985), U.S. Pat. No. 4,533,254, Mahew et al., *Methods In Enzymology*, Vol. 149, pp. 64-77 (1987), Mahew et al., *Biochimica et Biophysica Acta*, Vol. 75, pp. 169-174 (1984), and Cheng et al., *Investigative Radiology*, Vol. 22, pp. 47-55 (1987), and U.S. Ser. No. 428,339, filed Oct. 27, 1989. The disclosures of each of the foregoing patents, publications and patent applications are incorporated by reference herein, in their entirety. As a preferred technique, a solvent free system similar to that described in International Application PCT/US85/01161, or U.S. Ser. No. 428,339, filed Oct. 27, 1989, is employed in preparing the liposome constructions. By following these procedures, one is able to prepare liposomes having encapsulated therein a gaseous precursor or a solid or liquid contrast enhancing agent.

The materials which may be utilized in preparing the liposomes of the present invention include any of the materials or combinations thereof known to those skilled in the art as suitable in liposome construction. The lipids used may be of either natural or synthetic origin. Such materials include, but are not limited to, lipids such as cholesterol, cholesterol hemisuccinate, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids, polymerizable lipids, and combinations thereof. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art.

Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

In addition, the size of the vesicles can be adjusted by a variety of procedures including filtration, sonication, homogenization and similar methods to modulate liposomal biodistribution and clearance. To increase internal aqueous trap volume, the vesicles can be subjected to repeated cycles of freezing and thawing.

The liposomes employed may be of varying sizes, but preferably have a mean outer diameter between about 30 nanometers and about 10 microns. As is known to those skilled in the art, vesicle size influences biodistribution and, therefore, different size vesicles are selected for various purposes. For intravascular use, for example, vesicle size is generally no larger than about 2 microns, and generally no smaller than about 30 nanometers, in mean outer diameter. For non-vascular uses, larger vesicles, e.g., between about 2 and about 10 micron mean outside diameter may be employed, if desired.

The lipids employed may be selected to optimize the particular therapeutic use, minimize toxicity and maximize shelf-life of the product. Neutral vesicles composed of either saturated or unsaturated phosphatidylcholine, with or without sterol, such as cholesterol, function quite well as intravascular hyperthermia potentiators to entrap gas and perfluorocarbons. To improve uptake by cells such as the reticuloendothelial system (RES), a negatively charged lipid such as phosphatidylglycerol, phosphatidylserine or similar materials is added. For even greater vesicle stability, the liposome can be polymerized using polymerizable lipids, or the surface of the vesicle can be coated with polymers such as polyethylene glycol so as to protect the surface of the vesicle from serum proteins, or gangliosides such as GM1 can be incorporated within the lipid matrix. Vesicles or micelles may also be prepared with attached receptors or antibodies to facilitate their targeting to specific cell types such as tumors.

The gas, gaseous precursors, perfluorocarbons, and other hyperthermia potentiators can be encapsulated by the liposome by being added to the medium in which the liposome is being formed, in accordance with conventional protocol. Where gases are concerned, the procedures preferably employed are those techniques for encapsulating gases within a liposome described in applicant's copending application U.S. Ser. No. 569,828, filed on Aug. 20, 1990, the disclosures of which are hereby incorporated by reference in their entirety herein.

It should be noted that where pH sensitive gaseous precursors are encapsulated in liposomes, ionophores should be incorporated into the liposome membrane so that the gaseous precursors can more efficiently produce gas when exposed to a pH gradient. Indeed, it has been found that although liposomes are not impermeable to protons or hydroxide ions, the permeability coefficient of liposomes is generally so very low that it often takes weeks or months to dissipate a pH gradient. Providing a more rapid transport of hydrogen ions or hydroxide ions across a liposome membrane in order to activate pH-modulated gaseous precursors is necessary. The incorporation of ionophores in the liposome membrane, in accordance with the present invention, provides the necessary means of transporting the activating ions. By increasing the rate of hydrogen or hydroxide ion flux across the liposome membrane, such ionophores will increase the rate within the liposome of gas formation from the pH-activated gaseous precursor.

As used herein, the phrase "ionophore-containing liposome" denotes a liposome having incorporated in the membrane thereof an ionophore. The term "ionophore", as used herein, denotes compounds which are capable of facilitating the transport of ions across the liposome membrane to effect a change in pH inside the liposome membrane, and include compounds commonly referred to as proton carriers and channel formers.

Suitable ionophores include proton carriers such as nitro-, halo- and oxygenated phenols and carbonylcyanide phenylhydrazones. Preferred of such proton carriers are carbonylcyanide, p-trifluoromethoxyphenylhydrazone (FCCP), carbonylcyanide M-chlorophenylhydrazone (CCCP), carbonylcyanide phenylhydrazine (CCP), tetrachloro-2-trifluoromethyl benzimidazole (TTFB), 5,6-dichloro-2-trifluoromethyl benzimidazole (DTFB), and Uncoupler 1799 Suitable channel formers include gramicidin, alamethicin, filipin, etruscomycin, nystatin, pimaricin, and amphotericin. Other suitable proton carriers include the following compounds which preferably exhibit selectivity for cations, but will also transport protons and/or hydroxide ions: valinomycin, enniatin (type A, B or C), beauvericin, monomycin, nonactin, monactin, dinactin, trinactin, tetranactin, antamanide, nigericin, monensin, salinomycin, narisin, mutalomycin, carriomycin, dianemycin, septamycin, A-204 A, X-206, X-537 A (lasalocid), A-23187 and dicyclohexyl-18-crown-6. Such ionophores are well known in the art and are described, for example in Jain et al., *Introduction to Biological Membranes*, (J. Wiley and Sons, N.Y. 1980), especially pp. 192-231, and *Metal Ions In Biological Systems*, ed. H. Sygel, Vol. 19, "Antibiotics And Their Complexes" (Dekker, N.Y. 1985), disclosures of each of which are incorporated herein by reference in their entirety. The ionophores may be used alone or in combination with one another.

To incorporate ionophores into the liposome membrane, the ionophores, which are lipophilic, are simply added to the lipid mixture, and the liposomes are prepared in the usual fashion. They may also, if desired, be added after the liposome has been formed, and will spontaneously intercalate into the membrane.

Other methods of stabilizing the compounds of the invention, particularly the gases, are well known. For example, a material may be formulated as a closed membrane-bounded structure encompassing the enclosed gas bubble, examples of which include, but are not limited to polymeric microcapsules prepared by a variety of methodologies such as those disclosed in U.S. Pat. No. 4,898,734, polymer mixtures such as those described in U.S. Pat. No. 4,466,442, and albumin microspheres such as those disclosed in U.S. Pat. No. 4,718,433, the disclosures of each of which are incorporated herein by reference in their entirety. Such structures prevent or constrain the release of gas because either the entrapped gas bubble cannot physically pass through the intact membrane and/or the membranes have an intrinsically low permeability to the entrapped gas. Materials may also be formulated as a macroreticulated porous structures which serve to physically entrap the gas bubble within a highly cross-linked matrix. Examples of such systems include, but are not limited to, cross-linked dextran beads, silica aerogels or cross-linked proteinaceous structures. The nature of the cross-link may be physical, i.e., non-covalent, as in the physical entwining of long polymer fibers, or else may be chemical, i.e., covalent, as in, for example, the glutaraldehyde cross-linking of synthetic polyaminoacid chains. Such macroreticulated systems may be formulated as a hollow shell or as a filled structure. Micelle structures of lipids may also be employed. Finally, a material may be prepared for which the gas has a naturally high affinity and is either absorbed onto the surface or is soluble within the material of the structure. An example of the former includes, but is not limited to, carbon particles or low surface-tension surfactant particles onto which many gases absorb. Examples of the latter include an oil in water emulsion or coacervate, or silicone particles in which a gas such as nitrogen may preferentially dissolve. Such materials might preferably be prepared under high pressure, or over a certain range of temperature, in order to maximize the amount of gas either absorbed to or dissolved within the material.

The hyperthermic potentiators of the present invention are administered to a biological tissue or to biological fluids, whereupon ultrasound is then applied to the biological matter. The methods of the invention are particularly useful when employed in relation to such biological matter as tumor tissue, muscle tissue or blood fluids.

Where the usage is in vivo, administration may be carried out in various fashions, such as intravascularly, intralymphatically, parenterally, subcutaneously, intramuscularly, intraperitoneally, interstitially, hyperbarically or intratumorly using a variety of dosage forms, the particular route of administration and the dosage used being dependent upon the type of therapeutic use sought, and the particular potentiating agent employed. A gaseous hyperthermic potentiator, for example, may be injected directly into a tumor, with or without stabilization. To deliver the air bubbles to the tumor site using an intravascular administrative route, however, the air bubbles are preferably stabilized to avoid uptake by the pulmonary circulation. Where intraarterial injection of gas is used for delivery to a tumor, the air bubbles need not be as stable as in the case of peripheral intravascular injection. Perfluorocarbons are preferably administered either intravascularly or interstitially. Typically, dosage is initiated at lower levels and increased until the desired temperature increase effect is achieved. In tumors with a principal dominant arterial supply such as the kidney, these hyperthermic potentiating agents may be administered intra-arterially.

For in vivo usage, the patient can be any type of mammal, but most preferably is a human. The method of the invention is particularly useful in the treatment of tumors, various inflammatory conditions, and arthritis, especially in the treatment of tumors. The stabilized bubbles, gaseous precursors and perfluorocarbons accumulate in tumors, particularly in the brain, because of the leaky capillaries and delayed wash-out from the diseased tissues. Similarly, in other regions of the body where tumor vessels are leaky, the hyperthermic potentiating agents will accumulate.

The hyperthermic potentiators of the present invention may be used alone, or in combination with one another, such as in using perfluorocarbons in combination with gases. In addition, the potentiators of the invention may be employed in combination with other therapeutic and/or diagnostic agents. In tumor therapy applications, for example, the hyperthermic potentiators may be administered in combination with various chemotherapeutic agents.

Any of the various types of ultrasound imaging devices can be employed in the practice of the invention, the particular type or model of the device not being critical to the method of the invention. Preferably, however, devices specially designed for administering ultrasonic hyperthermia ar preferred. Such devices are described U.S. Pat. Nos. 4,620,546, 4,658,828 and 4,586,512, the disclosures of each of which are hereby incorporated herein by reference in their entirety.

Although applicant does not intend to be limited to any particular theory of operation, the hyperthermic potentiators employed in the methods of the present invention are believed to possess their excellent results because of the following scientific postulates.

Ultrasonic energy may either be transmitted through a tissue, reflected or absorbed. It is believed that the potentiators of the invention serve to increase the absorption of sound energy within the biological tissues or fluids, which results in increased heating, thereby increasing the therapeutic effectiveness of ultrasonic hyperthermia.

Absorption of sound is believed to be increased in acoustic regions which have a high degree of ultrasonic heterogeneity. Soft tissues and fluids with a higher degree of heterogeneity will absorb sound at a higher rate than tissues or liquids which are more homogeneous acoustically. When sound encounters an interface which has a different acoustic impedance than the surrounding medium, there is believed to be both increased reflection of sound and increased absorption of sound. The degree of absorption of sound is believed to rise as the difference between the acoustic impedances between the two tissues or structures comprising the interface increases.

Intense sonic energy is also believed to cause cavitation and, when cavitation occurs, this in turn is thought to cause intense local heating. Gas bubbles are believed to lower the cavitation threshold, that is, accelerate the process of cavitation during sonication.

Since gas bubbles and perfluorocarbons have high acoustic impedance differences between liquids and soft tissues, as well as decrease the cavitation threshold, the gas bubbles and perfluorocarbons may act to increase the rate of absorption of ultrasonic energy and effect a conversion of that energy into local heat. Additionally, the low thermal conductivity of gas may serve to decrease local heat dissipation, with the result that there is both an increase in the rate of heating and an increase in the final equilibrium temperature.

The potentiators of the present invention may serve to increase the acoustic heterogeneity and generate cavitation nuclei in tumors and tissues thereby acting as a potentiator of heating in ultrasonic hyperthermia. Because the gases and perfluorocarbons create an acoustic impedance mismatch between tissues and adjacent fluids, the perfluorocarbons and gas bubbles act similarly and increase the absorption of sound and conversion of the energy into heat.

The following examples are merely illustrative of the present invention and should not be considered as limiting the scope of the invention in any way. These examples and equivalents thereof will become more apparent to those versed in the art in light of the present disclosure, and the accompanying claims.

In all of the examples which follow, a 1.0 megahertz continuous wave ultrasonic transducer (Medco Mark IV Sonlator) was used to apply the ultrasonic energy. Degassing of the solution, that is, removal of the gas from the solution, was accomplished by using standard vacuum procedures.

Examples 1 through 7 are actual examples of the invention. Examples 8 through 16 are prophetic examples meant to be illustrative of how the invention would operate under the specified conditions.

EXAMPLES

EXAMPLE 1

A cooled degassed solution of phosphate buffered saline (PBS) was subjected to ultrasonic hyperthermia. Another equal volume of standard PBS was pressurized in a commercial soda syphon with carbon dioxide. The pressure was released and the solution was then subjected to ultrasound with identical parameters as for the previously described solution of PBS. The gassed solution reached a significantly higher temperature than the degassed solution. These results are illustrated in FIG. 1.

EXAMPLE 2

Figure 2:
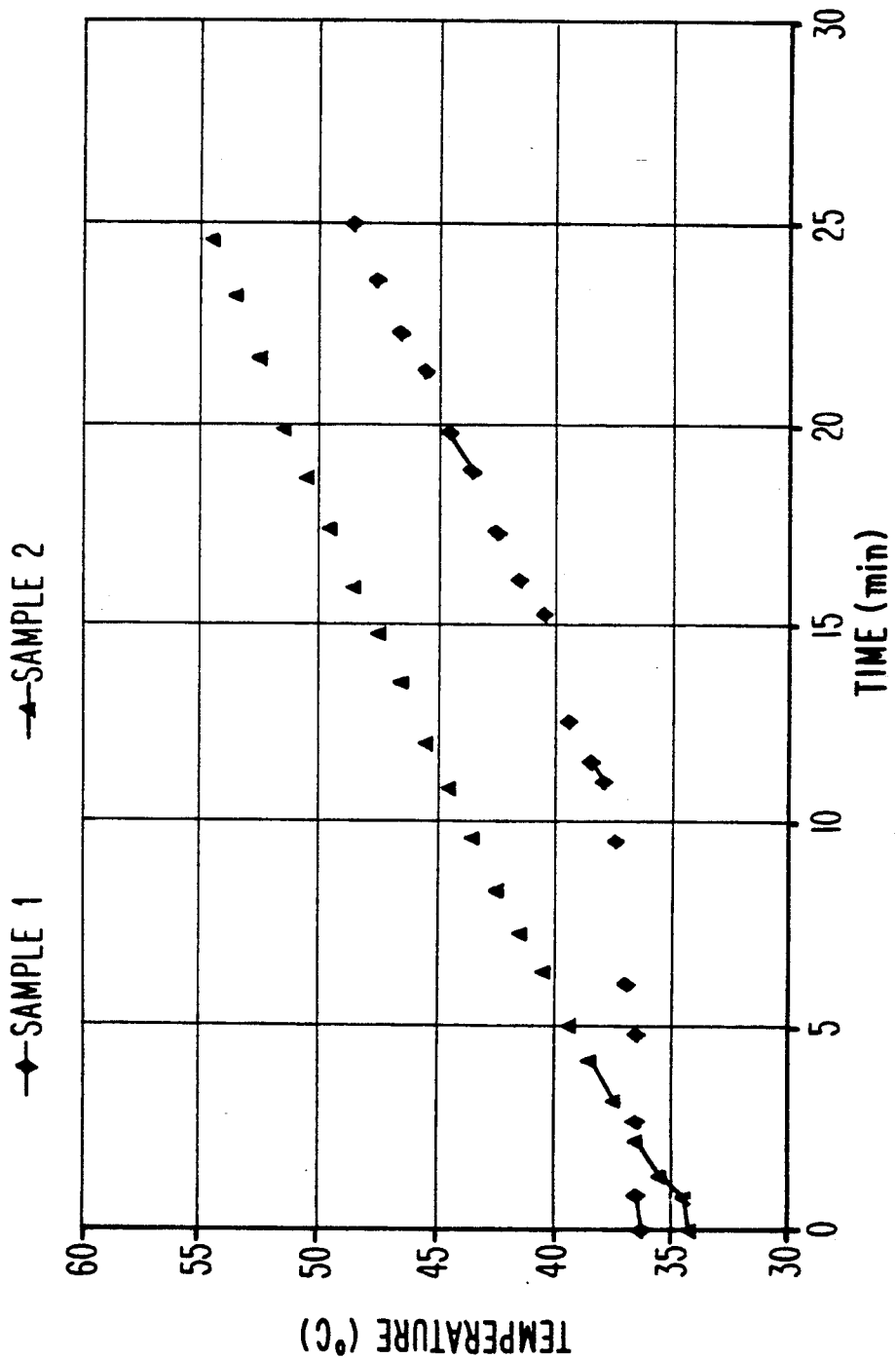
FIG. 2. This figure provides a graph which plots the temperature over time for two different samples subjected to ultrasound treatment using a 1.0 megahertz continuous wave source of ultrasonic energy. Sample 2 (a phosphate buffered saline solution pressurized with $CO_2$ gas) shows a much greater increase in temperature over time than Sample 1 (a degassed phosphate buffered saline solution).

Gas bubbles of nitrogen were passed through a standard solution of PBS. A degassed solution of PBS was prepared. Ultrasound energy was applied to each solution, during which time the temperature was measured with a thermometer. The solution containing gas bubbles (Sample 2) reached a significantly higher temperature than the degassed solution (Sample 1). The results in this example are shown in FIG. 2, and are qualitatively similar to those observed in Example 1.

In both Examples 1 and 2, it should be noted that the ultrasonic hyperthermia was commenced immediately after gasing the solutions. When ultrasonic hyperthermia was delayed more than five minutes after the gasing step, the resultant temperature was only slightly greater than for the degassed PBS. This is attributed to the relatively rapid decay of the non-stabilized gas bubbles in solution.

EXAMPLE 3

Liposomes encapsulating gas were prepared via a pressurization process as previously described in applicant's copending application, U.S. Ser. No. 569,828, filed Aug. 20, 1990. A liposome without gas was also prepared. The two samples were exposed to ultrasonic energy as described above. The results revealed improved heating for the liposomes that encapsulated the gas similar to that shown in FIG. 2. The gas, whether or not entrapped in an outer stabilizing covering such as a liposome, serves to potentiates the heating.

The advantage of using liposomes or other such stabilizing methods is that in vivo the stabilized bubbles may perhaps be more readily directed to sites, e.g., tumors than unencapsulated bubbles. Note that the nonencapsulated bubbles as described in Examples 1 and 2 were only stable for several minutes in solution, whereas the liposomal bubbles will have a much longer stability.

EXAMPLE 4

Albumin microspheres were prepared as previously described U.S. Pat. No. 4,718,433 to encapsulate air. Two solutions of PBS were prepared, one containing albumin microspheres encapsulating gas and the other containing a solution of the same concentration of albumin in degassed PBS. The concentration of albumin in both cases was 1%. Ultrasonic energy was then applied as in Example 1. The solution containing the gas filled albumin microspheres reached a significantly higher temperature than the solution of albumin without gas. The temperature increase observed for the gassed solution was similar to that observed for the samples containing gas described in Examples 1 through 3.

EXAMPLE 5

Stabilized air bubbles were prepared as previously described using a mixture of the polymers polyoxyethylene and polyoxypropylene as in U.S. Pat. No. 4,466,442 in solution. Ultrasonic energy was applied. Again, the temperature measurements showed a higher temperature for the solution containing the stabilized air bubbles.

EXAMPLE 6

A solution containing emulsions of perfluorooctylbromide (PFOB) was prepared as described in U.S. Pat. No. 4,865,836 (Sample 1), and the solution was exposed to ultrasonic hyperthermia. Additionally, a second solution of PFOB emulsion was prepared following the same procedures, except that this second solution was gassed with oxygen as described in U.S. Pat. No. 4,927,623 (Sample 2). Sample 2 was then exposed to ultrasonic hyperthermia. The Samples 1 and 2 containing the PFOB both achieved a higher temperature upon ultrasound treatment than the degassed PBS of Examples 1 and 2. In addition, Sample 2 reached an even higher temperature with ultrasonic hyperthermia than Sample 1.

EXAMPLE 7

A tissue equivalent phantom was prepared using low temperature agar gel with a 50° C. gelling temperature. A phantom was prepared from degassed PBS and 4% agar gel. Another phantom was prepared, but in this case the liquid gel was pressurized with nitrogen gas at 180 psi for 24 hours in a custom built pressurization chamber at 52° C. The pressure was released over a period of 5 seconds thus forming microbubbles in the liquid yet viscous gel. Both gel samples (degassed and that containing microbubbles) were allowed to gel and to cool to 37° C. The samples were then exposed to ultrasonic energy as above and the temperatures recorded. The sample containing microbubbles again had a much higher rate of heating than the gel prepared from the degassed solution.

The above was repeated but in this case liposomes entrapping gas were placed in the gel and the gel again cooled to 37° C. Ultrasonic heating again showed an improved rate of heating. The purpose of the tissue equivalent phantom was to demonstrate how the bubbles might potentiate heating in tissues, e.g., a tumor.

EXAMPLE 8

Two rats bearing C2 clonal derived epithelial carcinoma are treated with ultrasonic therapy. In one of these rats, 2 cc of nitrogen gas is injected into approximately 4 cc of tumor volume. Hyperthermia is administered to both rats and the intra-tumoral temperature monitored. The rat treated with an interstitial injection of nitrogen has a higher tumor temperature.

EXAMPLE 9

One group of rabbits bearing VX2 carcinoma of the brain are treated with ultrasonic hyperthermia while the tumor temperature and the temperature of the surrounding tissue is monitored with a probe. A volume of 3 to 5 cc of perfluorooctybromide emulsion is injected into a second group of rabbits in the carotid artery ipsilateral to the brain tumor, while monitoring the tumor and surrounding tissue. The rabbits treated with the PFOB show increased tumor temperatures and a more selective heating of the brain tumor as compared to the normal tissue.

EXAMPLE 10

The same experiment as in Example 9 is repeated using a 3 cc injection of liposomes encapsulating gas. Again temperature measurements of tumor and normal tissue show increased temperature in the tumor relative to normal tissue of the animal treated with the gas filled liposomes.

EXAMPLE 11

A solution of liposomes encapsulating the gaseous precursor methylactate is prepared and suspended in PBS. A control solution of PBS and the solution containing the liposomes encapsulating methylactate is heated with ultrasound and the temperature measured. The temperature of the solution containing the liposomes encapsulating methylactate has a biexponential rate of heating reflecting the improvement in heating efficiency past the point at which gas is formed from the gaseous precursor.

EXAMPLE 12

In a patient with cancer of the kidney, the left femoral artery is catheterized using standard technique. The renal artery is catheterized and 10 cc of a 1% solution of sonicated albumin microspheres entrapping gas is injected into the renal artery. Therapeutic ultrasound is used to heat the tumor and the microbubbles of gas delivered to the tumor cause improved tumor heating.

EXAMPLE 13

Example 12 is repeated in another patient but in this case gas bubbles encapsulated in the tensides polyoxyethylene and polyoxypropylene are used to embolize the kidney. Again therapeutic ultrasound is applied to the kidney and the result is improved heating of the tumor.

EXAMPLE 14

Example 13 is repeated but this time using liposomes encapsulating both chemotherapy and carbon dioxide gas. Again hyperthermia is applied to the tumor using ultrasound and not only is there improved tumor heating, but also improved tumor response caused by the interaction of simultaneous heating and chemotherapy.

EXAMPLE 15

Small liposomes, less than about 100 nm diameter, are prepared to entrap nitrogen gas under pressure. Phase sensitive lipids are selected with gel to liquid crystalline transition temperature of 42.5° C. These are administered intravenously to a patient with glioblastoma multiforme, which is a usually deadly brain tumor. Ultrasonic hyperthermia is applied to the region of the brain tumor through a skull flap which has been previously made surgically. The microbubbles entrapped in the liposomes accumulate in the patient's tumor because of the leakiness of the tumor vessels. The microbubbles are excluded from the normal brain because of the integrity of the blood-brain barrier. The ultrasonic energy raises the tumor temperature to 42.5 degrees centigrade and the liposomes underwent phase transition allowing the bubbles to expand. The intratumoral bubbles increases the effectiveness of heating in the tumor by the therapeutic ultrasound.

EXAMPLE 16

Air bubbles are entrapped in lipid monolayers as previously described in U.S. Pat. No. 4,684,479. In a patient with glioblastoma multiforme, these lipid monolayer stabilized air bubbles are administered I.V. every day for 7 days during daily treatments with ultrasonic hyperthermia. The stabilized air bubbles accumulate in the patient's tumor and the patient has improved response to treatment with ultrasonic hyperthermia.

Various modifications in addition to those shown and described herein will be apparent to those skilled in the art from the foregoing description. Such modifications are also intended to fall within the scope of the appended claims.

What is claimed is:

1. A method for heat treating biological tissues and fluids which comprises:
   (i) administering to the tissue or fluid to be treated a therapeutically effective amount of a hyperthermia potentiator selected from the group consisting of gas, gaseous precursors and perfluorocarbons; and
   (ii) applying ultrasound to heat said tissue or fluid to a temperature of at least about 43° C.

2. A method of claim 1 wherein said hyperthermia potentiator is selected from the group consisting of gas, gaseous precursors and perfluorocarbons.

3. A method of claim 2 wherein said hyperthermia potentiator is gas.

4. A method of claim 3 wherein said gas is selected from the group consisting of air, carbon dioxide, oxygen, nitrogen, xenon, argon, neon and helium.

5. A method of claim 3 wherein said gas consists of stabilized gas bubbles.

6. A method of claim 5 wherein said stabilized gas bubbles consist of stabilized air bubbles.

7. A method of claim 2 wherein said hyperthermia potentiator is a gaseous precursor.

8. A method of claim 7 wherein said gaseous precursor is selected from the group consisting of aminomalonate, sodium bicarbonate, methylactate and diazonium compounds.

9. A method of claim 2 wherein said hyperthermia potentiator is a perfluorocarbon.

10. A method of claim 9 wherein said perfluorocarbon is selected from the group consisting of perfluorooctyl iodide, perfluorotributylamine, trifluoropropylamine or perfluorooctlybromide.

11. A method of claim 1 wherein said hyperthermia potentiator is encapsulated in a liposome.

12. A method of claim 3 wherein said hyperthermia potentiator is encapsulated in a liposome.

13. A method of claim 7 wherein said hyperthermia potentiator is encapsulated in a liposome.

14. A method of claim 9 wherein said hyperthermia potentiator is encapsulated in a liposome.

* * * * *

UNITED STATES PATENT AND TRADEMARK OFFICE
CERTIFICATE OF CORRECTION

PATENT NO. : 5,149,319

DATED : September 22, 1992

INVENTOR(S) : Evan C. Unger

It is certified that error appears in the above-identified patent and that said Letters Patent is hereby corrected as shown below:

On the facing page, under U.S. PATENT DOCUMENTS, the following patents cited by Applicants on March 4, 1991 and considered by the Examiner on June 27, 1991, should be added:

| | | | |
|---|---|---|---|
| 4,927,623 | 5/22/90 | Long, Jr. | 424/5 |
| 4,442,843 | 4/17/84 | Rasor et al. | 128/660 |
| 4,681,119 | 7/21/87 | Rasor et al. | 128/660 |
| 4,844,882 | 7/4/89 | Widder et al. | 42/49 |
| 4,898,734 | 2/6/90 | Mathiowitz et al. | 424/426 |
| 4,466,442 | 8/21/84 | Hilmann et al. | 128/653 |
| 4,718,433 | 1/12/88 | Feinstein | 128/660 |
| 4,774,958 | 10/4/88 | Feinstein | 128/660.01 |
| 4,684,479 | 8/4/87 | D'Arrigo | 252/307 |
| 4,728,575 | 3/1/88 | Gamble et al. | 428/402.2 |
| 4,533,254 | 8/6/85 | Cook et al. | 366/176 |
| 4,737,323 | 4/12/88 | Martin et al. | 264/4.3 |
| 4,728,578 | 3/1/88 | Higgins et al. | 428/462 |
| 4,658,828 | 4/21/87 | Dory | 128/660 |

UNITED STATES PATENT AND TRADEMARK OFFICE
CERTIFICATE OF CORRECTION

PATENT NO. : 5,149,319
DATED : September 22, 1992
INVENTOR(S) : Evan C. Unger

It is certified that error appears in the above-indentified patent and that said Letters Patent is hereby corrected as shown below:

On the title page, under OTHER PUBLICATIONS,

Cheng et al., *Investigative Radiology*, 22: 47-55 (1987).

Fitzpatrick et al., *Inorganic Chemistry*, 13(3): 568-574 (1974).

Hope et al., *Biochimica et Biophysica Acta*, 812: 55-65 (1985).

Jain et al., *Introduction to Biological Membranes*, pp. 192-231 (J. Wiley and Sons, N.Y. 1980).

Mayer et al., *Biochimica et Biophysica Acta*, 858: 161-168 (1986).

Mayhew et al., *Methods in Enzymology*, 149: 64-77 (1987).

Mayhew et al., *Biochimica et Biophysica Acta*, 775: 169-174 (1984).

*Metal Ions in Biological Systems: Antibiotics and Their Complexes*, Vol. 19, Sigel, H., ed. (Marcel Dekker, N.Y. 1985).

Stelmashok et al., *Koordinatsionnaya Khimiya*, 3(4) 524-527 (1977).

Thanassi, J.W., *Biochemistry*, 9(3):525-532 (1970).

In column 8, line 8, "ar preferred" should read "are preferred".

UNITED STATES PATENT AND TRADEMARK OFFICE
CERTIFICATE OF CORRECTION

PATENT NO. : 5,149,319
DATED : September 22, 1992
INVENTOR(S) : Evan C. Unger

It is certified that error appears in the above-indentified patent and that said Letters Patent is hereby corrected as shown below:

On the title page, under FOREIGN PATENT DOCUMENTS,

GB 2193095 A   03/02/88   United Kingdom

WO86/00238   16/01/86   PCT

Signed and Sealed this

Twenty-third Day of November, 1993

Attest:

BRUCE LEHMAN

*Attesting Officer*   *Commissioner of Patents and Trademarks*